(12) United States Patent
Hirano et al.

(10) Patent No.: US 7,164,121 B2
(45) Date of Patent: Jan. 16, 2007

(54) ION ATTACHMENT MASS SPECTROMETRY METHOD

(75) Inventors: Yoshiki Hirano, Fuchu (JP); Yoshiro Shiokawa, Hachioji (JP)

(73) Assignee: Anelva Corporation, Fuchu (JP)

( * ) Notice: Subject to any disclaimer, the term of this patent is extended or adjusted under 35 U.S.C. 154(b) by 125 days.

(21) Appl. No.: 10/658,392

(22) Filed: Sep. 10, 2003

(65) Prior Publication Data
US 2004/0079876 A1 Apr. 29, 2004

(30) Foreign Application Priority Data
Sep. 10, 2002 (JP) ............................. 2002-264551

(51) Int. Cl.
*H01J 49/10* (2006.01)
(52) U.S. Cl. ...................... 250/282; 250/288
(58) Field of Classification Search ............... 250/282, 250/281, 288
See application file for complete search history.

(56) References Cited

U.S. PATENT DOCUMENTS 6,781,117 B1 * 8/2004 Willoughby et al. ........ 250/281
6,800,850 B1 * 10/2004 Hirano et al. ............... 250/288

FOREIGN PATENT DOCUMENTS

| JP | 06-011485 | 1/1994 |
|---|---|---|
| JP | 2001-174437 | 6/2001 |
| JP | 2001-351567 | 12/2001 |
| JP | 2001-351568 | 12/2001 |
| JP | 2002-124208 | 4/2002 |
| JP | 2002-170518 | 6/2002 |

OTHER PUBLICATIONS

R.V. Hodges et al., "Application of Alkali Ions in Chemical Ionization Mass Spectrometry", Analytical Chemistry, vol. 48, No. 5, pp. 825-829 (1976).
Daniel Bombick, et al., "Potassium Ion Chemical Ionization and other uses of an Alkali Thermionic Emitter in Mass Spectrometry". Analytical Chemistry, vol. 56, No. 3, pp. 396-402 (1984).
Toshihiro Fujii et al., "Chemical Ionization Mass Spectrometry with Lithium Ion Attachment to the Molecule", Analytical Chemistry, vol. 61, No. 9, pp. 1026-1029 (1989).
Toshihiro Fujii, "A Novel Method for Detection of Radical Species in the Gas Phase: Usage of the LI+ Ion Attachment to Chemical Species", Chemical Physics Letters, vol. 191, No. 1.2, pp. 162-168 (1992).
T. Faye et al., "Sodium Ion Attachment Reactions in an Ion Trap Mass Spectrometer", Rapid Communications in Mass Spectrometry, vol. 13, pp. 1066-1073 (2000).

* cited by examiner

*Primary Examiner*—Kiet T Nguyen
(74) *Attorney, Agent, or Firm*—Buchanan Ingersoll & Rooney PC

(57) ABSTRACT

An ion attachment mass spectrometry method causes positively charged metal ions generated in a metal ion generation region to attach to molecules of a measured gas in an attachment region to generate attached ions, and then performs mass spectrometry on the attached ions in a mass spectrometry region. In the method, further, a pressure of the attachment region is set so as to be included in a pressure range enabling free flight of the metal ions and the attached ions in the attachment region, an electrostatic field is formed for decelerating the metal ions in the attachment region, and only the measured gas is introduced to the attachment region. Thereby, quantitative analysis enabling accurate measurement of the concentration of the measured gas is realized.

9 Claims, 3 Drawing Sheets

ION ATTACHMENT MASS SPECTROMETRY METHOD

BACKGROUND OF THE INVENTION

1. Field of the Invention

The present invention relates to an ion attachment mass spectrometry method, more particularly, relates to an ion attachment mass spectrometry method for quantitative analysis enabling accurate measurement of the concentration of a measured gas, and apparatus used therefor.

2. Description of the Related Art

Ion attachment mass spectrometry (IAMS) is a method of ionizing the molecules of a measured gas without causing fragmentation, making the ions of the molecules move to the mass spectrometry region, and analyzing their mass there.

Examples of apparatuses related to ion attachment mass spectrometry are disclosed in JP-A-6-11485, JP-A-2001-174437, JP-A-2001-351567, JP-A-2001-351568, JP-A-2002-124208, and JP-A-2002-170518. Further, as other documents, (1) Hodge, "Analytical Chemistry", 1976, vol. 48, no. 6, p. 825, (2) Bombick, "Analytical Chemistry", 1984, vol. 56, no. 3, p. 396, (3) Fujii, "Analytical Chemistry", 1986, vol. 61, no. 9, p. 1026, (4) Fujii, "Chemical Physics Letters", 1992, vol. 191, no. 1.2, p. 162, and (5) Fujii, "Rapid Communication in Mass Spectrometry", 2000, vol. 14, p. 1066 may be mentioned.

Referring to FIG. 6, the general configuration of an apparatus for ion attachment mass spectrometry will be explained. In FIG. 6, 1 indicates a metal ion generation region, 2 an attachment region, and 3 a mass spectrometry region. A differential exhaust region 4 is provided between the attachment region 2 and mass spectrometry region 3. The metal ion generation region 1 is provided with an emitter 11 and a repeller 12. Further, 21 indicates a mechanism for introduction of measured gas or sample gas, while 22 indicates a mechanism for introduction of an adjustment gas. The measured gas and the adjustment gas are introduced into the attachment region 2. Partitions 23 and 41 respectively having apertures 23a and 41a at their centers are provided between the attachment region 2 and differential exhaust region 4 and between the differential exhaust region 4 and the vacuum analysis region 3 respectively. A container part forming the attachment region is provided with a vacuum pump 24 and pressure gauge 25. The container part forming the mass spectrometry region is provided with a mass spectrometer 31 and vacuum pump 32. Further, the differential exhaust region 4 is provided with an exclusive vacuum pump 42.

In the ion attachment mass spectrometry apparatus of the above related art, all of the metal ion generation region 1, the attachment region 2, the mass spectrometry region 3, and the differential exhaust region 4 are at reduced pressure of not more than atmospheric pressure. In the metal ion generation region 1, an emitter 11 of an oxide of an alkali metal is heated to generate $Li^+$ and other positively charged metal ions. The metal ions are transported to the attachment region 2 from the metal ion generation region 1 by the repulsion force of the repeller 12.

The measured gas is introduced into the attachment region 2. In the attachment region 2, the metal ions gently attach to locations with a concentration of charges of molecules of the measured gas. The molecules to which the metal ions are attached become positively charged ions as a whole, whereby attached ions are generated. At the time of attachment, the surplus energy is extremely small, so disassociation does not occur.

However, to stabilize the attached ions so that the metal ions do not again disassociate from the molecules, it is necessary to strip the surplus energy by having the ions strike the ambient gas. To secure the maximum efficiency of stripping of the surplus energy, the pressure of the attachment region 2 of the related art is made about 100 Pa. The measured gas can be a gas for stripping the surplus energy, but usually the low reactivity $N_2$ gas etc. is separately introduced as the adjustment gas.

The adjustment gas also has another important role of decelerating the metal ions. To efficiently emit the metal ions from the emitter 11 and transport them to the attachment region 2, a translational energy of at least 10 eV is required in the metal ions. If the translational energy is high, even if the metal ions contact the molecules, they will not attach to the molecules, but will end up being reflected and running away without being ionized. Therefore, the metal ions emitted and transported with the high translational energy are made to strike the ambient gas at the attachment region 2 a large number of times to make them decelerate. For sufficient deceleration, the pressure of the attachment region 2 should be about 100 Pa.

The attached ions are transported to the mass spectrometry region 3 and are separated in mass and the intensity is measured by a Q-pole type mass spectrometer or other mass spectrometer 31 using electromagnetic force. The mass spectrometer 31 can only operate under a pressure of not more than $10^{-3}$ Pa, so the partitions 23 and 41 are provided between the attachment region 2 and mass spectrometry region 3 for creating a pressure difference.

FIG. 6 shows a general example of the related art. In an actual example of the related art, there is a partial difference from the above-mentioned related art of FIG. 6 due to the presence or absence of the differential exhaust region or vacuum pump. In addition, in each example of the related art, there are the following characteristic differences. In the document (1), the attached ions are made intermittently (pulses) by the fast changing electric field and the signal detected by a lock-in amplifier. Further, the adjustment gas containing a slight amount of the measured gas is introduced into the attachment region and the pressure made not more than 6 Pa. For this adjustment gas, the reaction gas is used and made to react once with metal ions, then the metal ions are shifted from the reaction product to the measured gas. In the document (2), $K^+$ is used as the metal ions and the pressure is made at least 2.4 Pa. In the document (5), the adjustment gas (He gas) of 0.1 Pa and the measured gas of $5 \times 10^{-3}$ are introduced into the attachment region. However, since an ion trap mass spectrometer using an internal ionization system is employed, the attachment region and mass spectrometry region are in the same region, the metal ions attach to the measured gas in the process of vibration due to the high frequency field, and the attached ions become unstable in vibration and are emitted to the detector.

According to the conventional ion mass spectrometry method, in each case, ionization is possible without causing disassociation of the molecules of the measured gas, and the ingredients of the measured gas (qualitative analysis) can be measured by a high accuracy. This surpasses other analytical methods of the ionization system. Much is expected for the ion attachment mass spectrometry method from the scientific and industrial viewpoints.

However, according to the ion attachment mass spectrometry method, there are the following three problems (1) to (3) directly relating to the measurement of the concentration of ingredients (quantitative analysis).

(1) The stability and reproducibility of the signal are poor.
(2) The linearity is poor. That is, an accurate proportional relationship cannot be established between the concentration of the measured gas and signal intensity. (3) The measured gas cannot be measured in a state of only the measured gas, that is, without the introduction of the adjustment gas.

Further, the ion attachment mass spectrometry method suffers from the following three problems (4) to (6) relating indirectly to the measurement of concentration of the ingredients (quantitative analysis).

(4) The apparatus is large in size and quality change of the measured gas in the apparatus may be possible. (5) A plurality of vacuum pumps is required and stable evacuation of the measured gas is difficult to secure. (6) Light and volatile matter enter the mass spectrometry region from the emitter and inhibit stable measurement.

OBJECTS AND SUMMARY

An object of the present invention is to provide an ion attachment mass spectrometry method suitable for quantitative analysis enabling accurate measurement of the concentration of the measured gas.

The ion attachment mass spectrometry method according to embodiments of the present invention is configured as follows for achieving the above object.

This ion attachment mass spectrometry method is a method causing positively charged metal ions generated in a metal ion generation region to attach to molecules of a measured gas in an attachment region to generate attached ions and then performing mass spectrometry of the attached ions in a mass spectrometry region. A characteristic point is that a pressure of the attachment region is set so as to be included in a pressure range enabling free flight of the metal ions and the attached ions in the attachment region, an electrostatic field is formed for decelerating the metal ions in the attachment region, and only the measured gas is introduced to the attachment region.

In the above method, preferably, an upper limit of the pressure range relating to the pressure of the attachment region is 10 Pa.

In the above method, more preferably, the metal ions traveling in the attachment region have translational energy not exceeding 1 eV.

In the above method, preferably, a partition is provided between the metal ion generation region and the attachment region, and the pressure of the metal ion generation region is made lower than the pressure of the attachment region.

In the above method, preferably, the metal ion genaration region and the mass spectrometry region are configured in a common region vacuum environment.

In the above method, preferably, a path of travel of ions in the attachment region is formed as a curved path.

In the above method, preferably, all of the metal ion generation region, attachment region, and mass spectrometry region are evacuated by a single common vacuum pump.

BRIEF DESCRIPTION OF THE DRAWINGS

The objects and features of the present invention will become clearer from the following description of the preferred embodiments given with reference to the attached drawings, in which.

DESCRIPTION OF THE PREFERRED EMBODIMENTS

Figure 1:
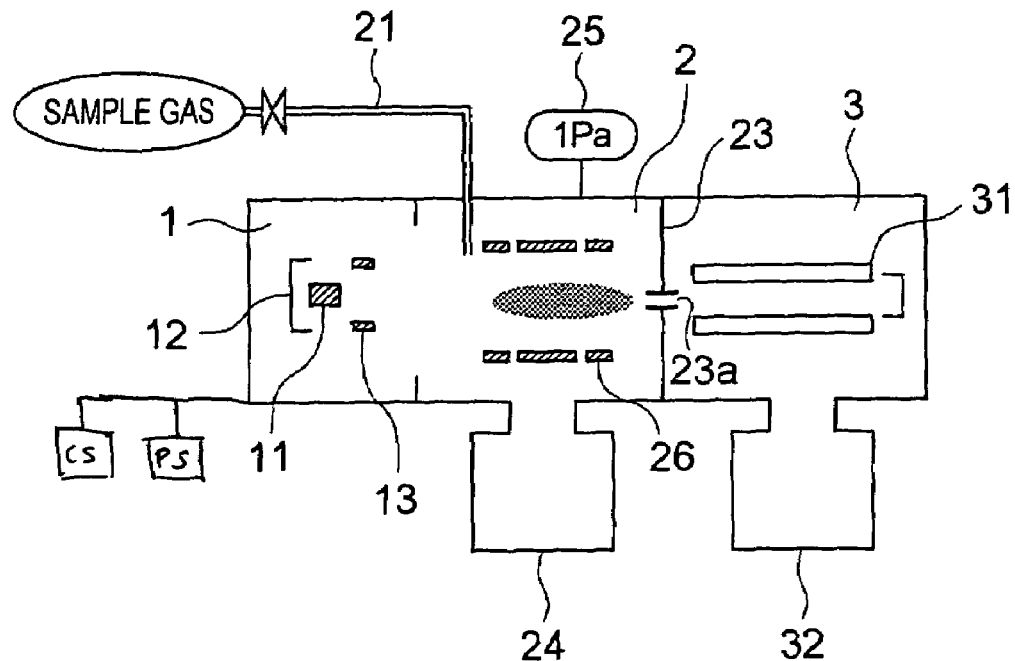
FIG. 1 is a longitudinal sectional view schematically showing the internal structure of an apparatus for working an ion attachment mass spectrometry method according to a first embodiment of the present invention.

At first, before explaining embodiments, the fundamental action or function realizing the present invention will be explained in the following. In the first place, the reasons for the problems mentioned above are explained. The problems of (1) the stability and reproducibility and (2) the linearity result from the pressure of the attachment region being 100 Pa in the method of the related art. With the pressure of 100 Pa, the average distance which the $Li^+$ can fly without striking the molecules of the ambient gas, or length of mean free path of about 0.1 mm. That is, when the $Li^+$ advances 10 mm, it will strike the molecules of the ambient gas as many as 100 times. This large number of strikes is helpful in stripping the surplus energy and deceleration, but inhibits the smooth advance of the metal ions. That is, the metal ions are decelerated by striking the molecules of the ambient gas and proceed in a zigzag fashion. In this state, since the metal ions can only move along the lines of force of the electrical field, control of the metal ions by an electrostatic lens becomes difficult. Further, in the low speed state, since the time during which the ions approach each other becomes longer, scattering of the metal ions occurs due to the mutual electrical repulsion force (space charge effect). These problems similarly hold true for attached ions.

Under the above conditions, the signal intensity fluctuates widely depending on the pressure, ingredients, flow of gas, etc. In particular, the space charge is extremely unstable, so the stability and reproducibility of the signal intensity are greatly obstructed. Further, the very existence of the ions affects these, so linearity can no longer be secured. Further, the effects also depend on the mass of the molecules, so the signal includes an unstable mass dependency. In actuality, in the electron impact method, which has problems in fragmentation, but is superior in stability, reproducibility and linearity, the ambient pressure is not more than $10^{-3}$ Pa.

The problems of (3) the adjustment gas, (4) the apparatus size, and (5) the number of pumps are also derived from the 100 Pa. If the pressure of the measured gas is less than 100 Pa, fundamentally, it is not possible to directly introduce only the measured gas without an adjustment gas. In order to connect the attachment region of the pressure of 100 Pa and the mass spectrometry region of the pressure of not more than $10^{-3}$ Pa and secure a diameter of the aperture of the partition not greatly obstructing the transport of attached ions, it is necessary to prepare a plurality of large vacuum pumps. Inevitably, the apparatus also becomes larger in size.

Considering the above reasons, in the present invention, the problems relating to quantitative analysis by the ion attachment mass spectrometry apparatus are solved by reducing the pressure in the attachment region to a predetermined level. That is, the pressure of the attachment region is made one in a range of pressure enabling free flight of the metal ions etc., for example, is made not more than 10 Pa. By making the pressure of the attachment region not more than 10 Pa, the ions will advance without striking the ambient gas and the space charge effect will not occur, so free flight becomes possible. High precision control of the acceleration, deceleration, concentration, etc. due to the electrostatic lens also becomes possible. Further, since the pressure difference becomes smaller, the number of vacuum pumps can also be reduced. So long as the pressure of the measured gas is higher than the attachment region, it becomes possible to measure only the measured gas.

On the other hand, if the pressure of the attachment region falls, the effect of stripping of the surplus energy and deceleration of the metal ions becomes weaker. The ratio of reduction of the surplus energy is of an extent substantially proportional to the pressure, but the deceleration sharply drops exponentially in pressure, so becomes a critical problem.

Therefore, an electrostatic field generating a force in the opposite direction to the advancing direction is formed in the attachment region to decelerate the metal ions by electric field. In the state where the pressure is low and the metal ions are able to travel by free flight, high precision control is possible by the electrostatic lens, so the metal ions are decelerated and then accelerated and concentrated efficiently at the required location without causing scattering. The degree of freedom of movement of the ions is raised.

Note that the above document (1) disclosed to make the pressure in the attachment region not more than 6 Pa, but since a synchronous wave detection system using a fast changing electric field is employed, only a relative signal affected by mass dependency is obtained. Further, since a reactive adjustment gas is used, the possibility of reaction and change in the measured gas is high. Further, the above document (2) also shows the use of 2.4 Pa, but uses $K^+$ having a large diameter and mass as the metal ion, so sufficient free flight is not achieved. The document (5) mentions 0.1 Pa as well, but due to the use of an ion trap mass spectrometer, so only a relative signal influenced by the mass dependency due to the high frequency electric field can be measured. Further, the adjustment gas (He gas) is also required for normal operation.

According to an embodiment of the present invention, with the ion attachment mass spectrometry method, the pressure of the attachment region is set so as to be included in the range of pressure enabling free flight of the metal ions and attached ions in the attachment region, an electrostatic field decelerating the travel of the metal ions is formed in the attachment region, and only measured gas is introduced into the attachment region, so it is possible to accurately measure the concentration of the measured gas. This is optimal for quantitative analysis.

Figure 6:
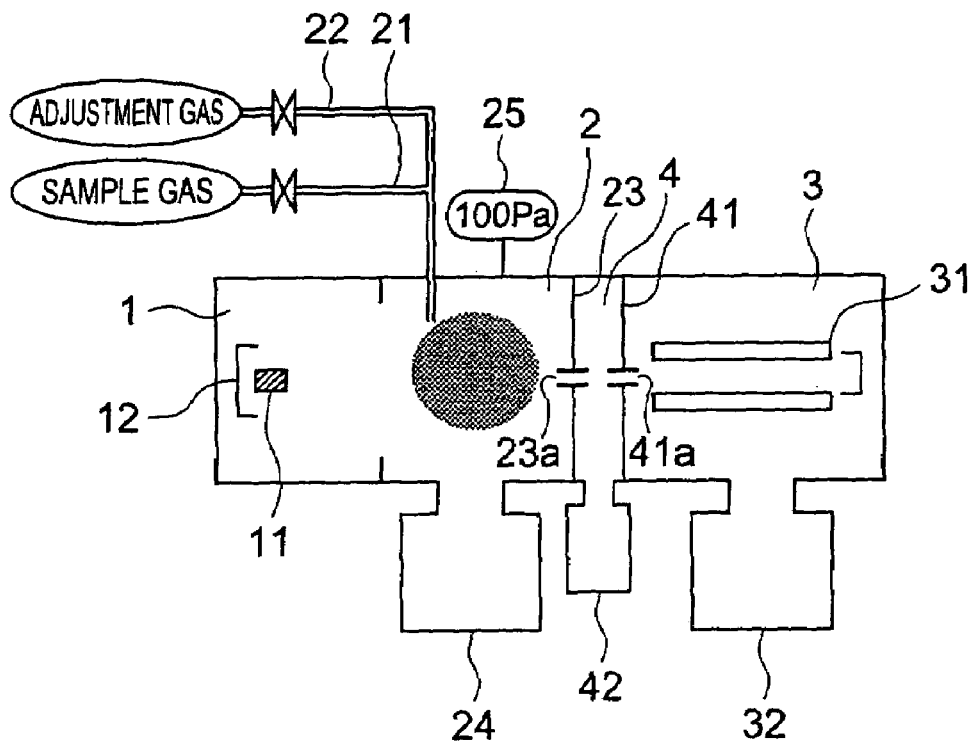
FIG. 6 is a longitudinal sectional view schematically showing the internal structure of an apparatus for working an ion attachment mass spectrometry method according to the related art.

Next, a preferred embodiment of the present invention will be explained with reference to the attached drawings. FIG. 1 is a longitudinal sectional view schematically showing the internal structure of an apparatus working the ion attachment mass spectrometry method according to a first embodiment of the present invention. In FIG. 1, components substantially the same as the components explained in FIG. 6 are assigned the same reference numerals.

In the ion attachment mass spectrometry apparatus shown in FIG. 1, 1 is a metal ion generation region, 2 an attachment region, and 3 a mass spectrometry region. The metal ion generation region 1 is provided with an emitter 11. A repeller 12 is arranged at the rear side of the emitter 11, while an extracting electrode 13 is arranged at the front side of the emitter 11. The metal ion generation region 1 and attachment region 2 are formed so that the vacuum environment forms a common space. At the attachment region 2, a tubular electrostatic lens 26 is arranged. A path of travel of ions is formed at the space inside the electrostatic lens 26. The attachment region 2 is provided with a mechanism 21 for introduction of the measured gas (or sample gas). Due to the introduction mechanism 21, the measured gas is introduced at a location at the inlet side of the electrostatic lens 26 in the attachment region 2. The attachment region 2 is provided with a pressure gauge 25 that measures the internal pressure. A partition 23 formed with an opening aperture 23a at the center is provided between the attachment region 2 and mass spectrometry region 3. The mass spectrometry region 2 is provided with a mass spectrometer 31. In the above ion attachment mass spectrometry apparatus, the container part of the attachment region 2 and the container part of the mass spectrometry region 3 are provided with vacuum pumps 24 and 32, respectively.

Note that in FIG. 1, the power system and the control system for giving a required current or voltage to the emitter 11, repeller 12, extracting electrode 13, and electrostatic lens 26 are schematically illustrated as PS and CS, respectively.

The static electric fields in the metal ion generation region 1 and attachment region 2 are formed by the extracting electrode 13 and the electrostatic lens respectively. The metal ion generation region 1 and the attachment region 2 form a common vacuum space. Due to the introduction mechanism 21, only measured gas is introduced to the attachment region 2 without any adjustment gas. The pressure there is 1 Pa or so. As the metal ions, for example, $Li^+$ is used. The average free flight of the $Li^+$ at 1 Pa is about 10 mm and the typical dimensions of the metal ion generation region 1 and attachment region 2 are several tens of mm or so, so the $Li^+$ strikes on an average only several times and sufficient free flight is performed.

As explained above, at the metal ion generation region 1 and the attachment region 2, the movement of the ions is in a manner of free flight, so the metal ions and the attached ions are reliably controlled by the electrostatic field. The metal ions efficiently taken out from the emitter 11 by the extracting electrode 13 are concentrated near the axis by the electrostatic lens 26 and decelerated down to not more than 1 eV. The metal ions with the lowered translational energy efficiently attach to the molecules of the measured gas, whereby attached ions are formed.

Next, the attached ions are again accelerated and concentrated and then transported to the mass spectrometry region 3. The mass spectrometry region 3 has a pressure of $10^{-3}$ Pa, but the pressure of the attachment region 2 is low, so there is no differential exhaust region like in the related art and the diameter of the aperture 23a of the partition 23 through which the attached ions pass is also larger. Due to this, the attached ions are efficiently transported to the mass spectrometry region 3.

In comparison of the ion attachment mass spectrometry method of the first embodiment with the example of the related art, the pressure of the attachment region 2 is low, so the efficiency of stripping the surplus energy is low, but the embodiment is superior in the points of efficiency of concentration and transport, so there is no great difference in terms of sensitivity. In addition, with the ion attachment mass spectrometry method according to the first embodiment, the stability, reproducibility, and linearity of the signal are greatly improved by the contribution of the free flight. Further, the number of vacuum pumps is reduced and the apparatus becomes smaller in size, so the distance from the measured region can be made shorter or direct connection becomes possible and therefore the problem due to sampling can be alleviated. So long as the measured gas has a pressure of at least 1 Pa, the measured gas can be measured alone without any adjustment gas.

Figure 2:
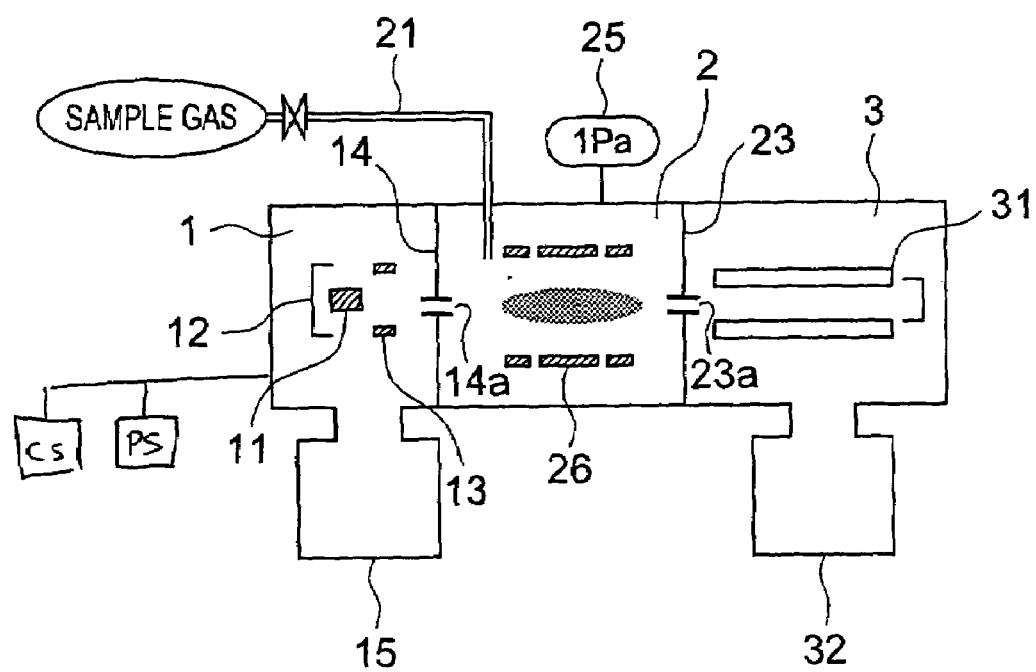
FIG. 2 is a longitudinal sectional view schematically showing the internal structure of an apparatus for working an ion attachment mass spectrometry method according to a second embodiment of the present invention.

Next, a second embodiment of the present invention will be explained with reference to FIG. 2. FIG. 2 is a vertical sectional view schematically showing the internal structure of an apparatus working the ion attachment mass spectrometry method according to the second embodiment of the present invention. In FIG. 2, components which are substantially the same as components explained in FIG. 1 are assigned the same reference numerals and detailed explanations are omitted. Below, the characteristic features of the second embodiment will be explained.

In the second embodiment, a partition 14 is provided between the metal ion generation region 1 and the ion attachment region 2. The metal ion generation region 1 and the attachment region 2 are formed as different regions and are connected through the center aperture 14a of the partition 14. The vacuum pump 15 is attached to the container part of the metal ion generation region 1. The rest of the configuration is the same as in the first embodiment.

In the second embodiment, a partition 14 is provided between the metal ion generation region 1 and the ion attachment region 2, and the attachment region is evacuated to a vacuum from the metal ion generation region 1. The front surface of the emitter 11 becomes a high temperature due to the action of current conduction from the power system, so the amount of metal ions generated due to the reaction with the measured gas fluctuates and disadvantages may occur in quantitative analysis. Therefore, in the present embodiment, for an attachment region 2 set to a pressure of 1 Pa, the pressure in the metal ion generation region 1 is set to $10^{-3}$ Pa due to the partition 14 and vacuum pump 15. Due to this, it is possible to greatly reduce the fluctuation of the amount of metal ions even in the case of a measured gas of a high reactivity.

Note that the metal ions have to pass through the aperture 14a of the partition 14, but this does not result in a large loss due to the effect of the extracting electrode 13. There is no vacuum pump directly evacuating the attachment region 2. The measured gas is evacuated from the apertures 14a and 23a of the two partitions 14 and 23. If this becomes a problem from the viewpoint of the object of measurement, it is possible to set another vacuum pump in the attachment region 2.

Figure 3:
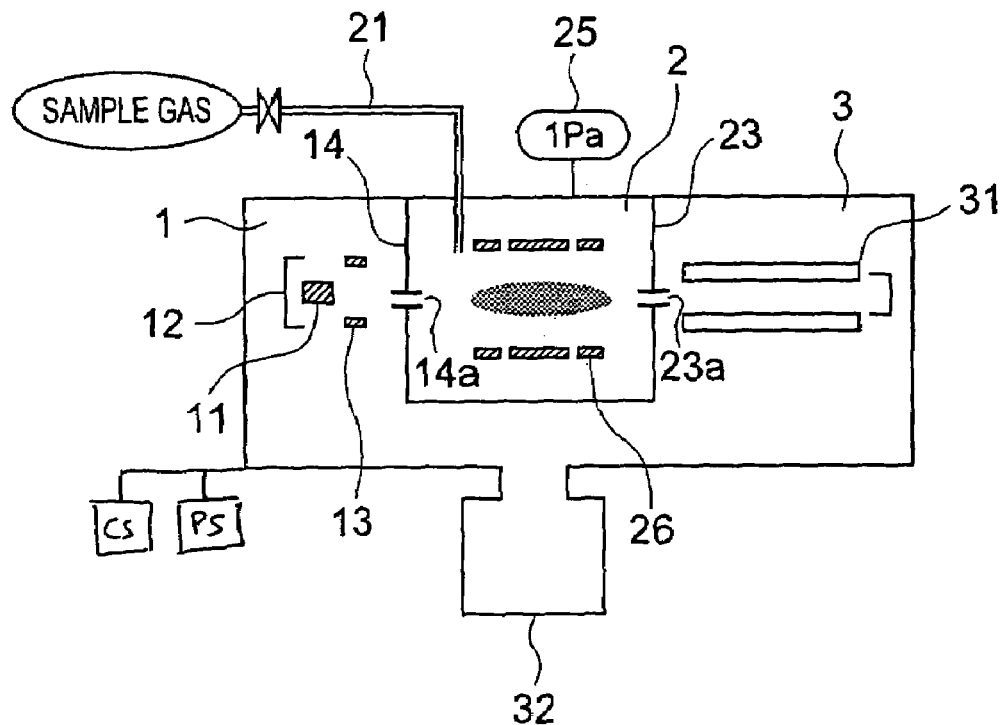
FIG. 3 is a longitudinal sectional view schematically showing the internal structure of an apparatus for working an ion attachment mass spectrometry method according to a third embodiment of the present invention.

Next, a third embodiment of the present invention will be explained with reference to FIG. 3. FIG. 3 is a vertical sectional view showing schematically the internal structure of an apparatus working the ion attachment mass spectrometry method according to the third embodiment of the present invention. In FIG. 3, components which are substantially the same as components explained in FIG. 1 and FIG. 2 are assigned the same reference numerals and detailed explanations are omitted. Below, the characteristic features of the third embodiment will be explained.

In the third embodiment, the attachment region 2 is formed as an independent chamber using two partitions 14 and 23, and the metal ion generation region 1 and mass spectrometry region 3 are connected to form a single common space. The common space of the metal ion generation region 1 and mass spectrometry region 3 is provided with the above vacuum pump 32. The rest of the configuration is the same as in the first and second embodiments.

As explained above, the metal ion generation region 1 and the mass spectrometry region 3 form a common vacuum space and only a single vacuum pump 32 is provided. According to this embodiment, the attachment region 2 of the pressure of 1 Pa is set so that the pressure of the metal ion generation region 1 and the mass spectrometry region 3 becomes $10^{-3}$ Pa. Due to this, it is possible to stabilize the amount of metal ions and reduce the number of pumps.

Figure 4:
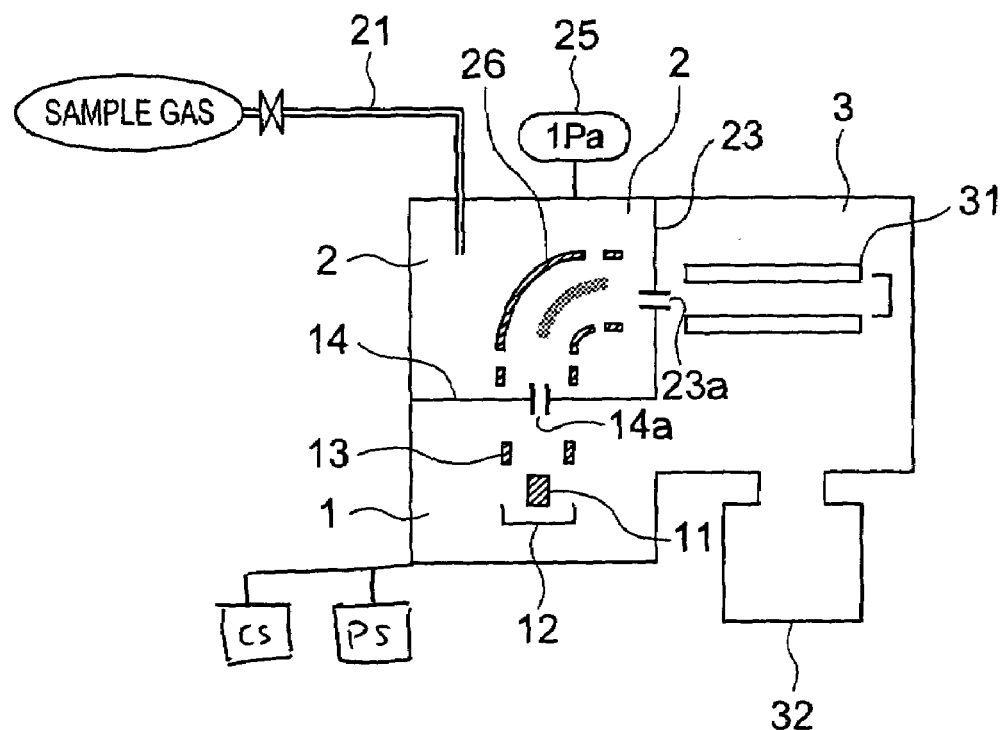
FIG. 4 is a longitudinal sectional view schematically showing the internal structure of an apparatus for working an ion attachment mass spectrometry method according to a fourth embodiment of the present invention.

Next, a fourth embodiment of the present invention will be explained with reference to FIG. 4. FIG. 4 is a vertical sectional view showing schematically the internal structure of an apparatus working the ion attachment mass spectrometry method according to the fourth embodiment of the present invention. The fourth embodiment is a modification of a third embodiment. In FIG. 4, components which are substantially the same as the components explained in the above embodiments are assigned the same reference numerals and detailed explanations are omitted. Below, the characteristic features of the fourth embodiment will be explained.

In the configuration of the fourth embodiment, compared with the third embodiment, the metal ion generation region 1 and the mass spectrometry region 3 are arranged in a perpendicular positional relationship with respect to the compartment part forming the attachment region 2, and the electrostatic lens 26 provided in the attachment region 2 is formed in a curved shape so as to be bent by 90 degrees. The partitions 14 and 23 forming the chamber of the attachment region 2 are arranged in a perpendicular positional relationship. The rest of the configuration is the same as in the third embodiment.

When performing measurement at a high precision in an ion attachment mass spectrometry apparatus, the light or volatile matter emitted from the emitter 11 enters the mass spectrometer 31 and sometimes causes a problem. Therefore, according to the configuration of the present embodiment, in the attachment region 2, the metal ions and attached ions curve due to the electrostatic field of the electrostatic lens 26 having the curved shape and therefore can be measured normally, but light and charge-free volatile matter proceeds straight, so it becomes possible to prevent them from entering the mass spectrometer. Note that the free flight ions can be easily made to curve by a suitable electrostatic field.

Figure 5:
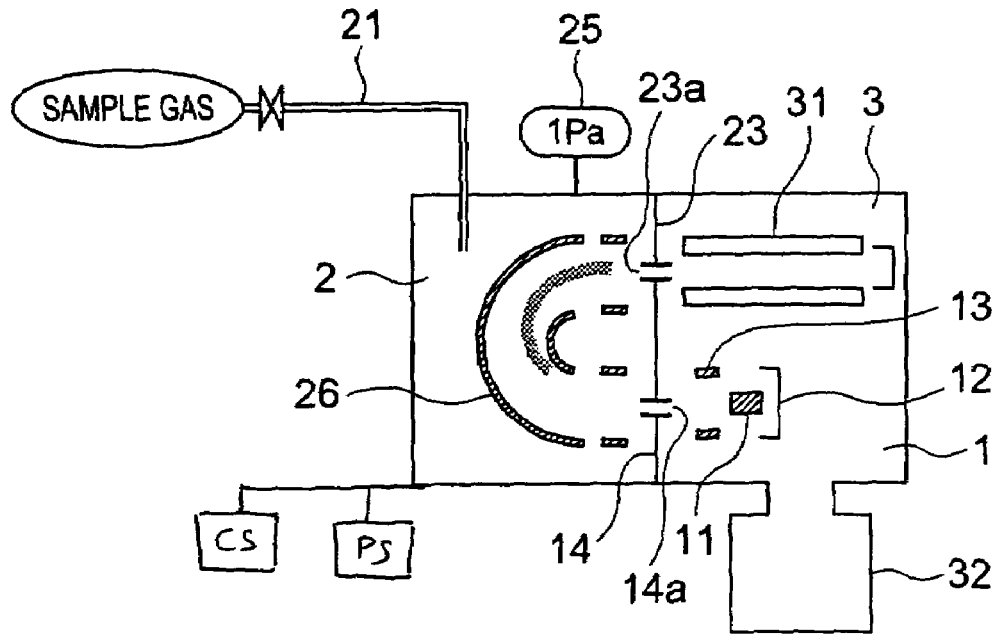
FIG. 5 is a longitudinal sectional view schematically showing the internal structure of an apparatus for working an ion attachment mass spectrometry method according to a fifth embodiment of the present invention.

Next, a fifth embodiment of the present invention will be explained with reference to FIG. 5. FIG. 5 is a vertical sectional view showing schematically the internal structure of an apparatus working the ion attachment mass spectrometry method according to the fifth embodiment of the present invention. The fifth embodiment is a further modification of the third embodiment. In FIG. 5, components which are substantially the same as components explained in the above embodiments are assigned the same reference numerals and detailed explanations thereof are omitted. Below, the characteristic features of the fifth embodiment will be explained.

In the configuration of the fifth embodiment, compared with the third embodiment, the metal ion generation region 1 and mass spectrometry region 3 are arranged in a parallel positional relationship. As a result, the partitions 14 and 23 are formed as a common partition. The electrostatic lens 26 placed in the attachment region 2 is configured having a curved form so as to be bent by 180 degrees from the aperture 13*a* to the aperture 23*a*. The path of travel in the electrostatic lens 26 is formed as a path curved by 180 degrees. The rest of the configuration is the same as the configuration of the third embodiment. According to the fifth embodiment, it is possible to make the apparatus even more compact.

The above-described embodiments can optionally be modified in the following way.

The pressure in the attachment region was 1 Pa, so the length of mean free path is about 10 mm, but may be any pressure enabling free flight of the metal ions and attached ions. Strictly speaking, the translational energy of the ambient gas is 0.04 eV, there is still a large difference compared with decelerated metal ions, so substantial free flight can be maintained during about 10 collisions. Further, the distance which ions are able to fly without striking the ambient gas has energy dependence. 1% of the total can proceed a distance of about 5 times of the length of mean free path. Therefore, the typical dimension of the attachment region is estimated to be 50 mm or slightly smaller. Even if the pressure of the attachment region is made 10 Pa so the length of mean free path is about 1 mm, 1% of the ions will travel by free flight. Therefore, from the viewpoint of practical use, as the range of a two-digit drop in sensitivity, the pressure to which the present invention can be applied may preferably be deemed to be a maximum of 10 Pa. Incidentally, with the configuration of the apparatus of the related art, it is known that if the pressure of the attachment region is lowered from the usual 100 Pa to 10 Pa, the signal intensity becomes 1/100.

As the metal ions, $Li^+$ was used, but the invention is not limited to this. It is also possible to use $K^+$, $Na^+$, $Rb^+$, $Cs^+$, $Al^+$, $Ga^+$, $In^+$, etc. Further, as the mass spectrometer, use was made of a Q-pole mass spectrometer, but the invention is not limited to this. It is also possible to use an ion trap mass spectrometer using the external ionization system, a magnetic field sector mass spectrometer, a TOF (time of flight) mass spectrometer, or an ICR (ion cyclotron resonance) mass spectrometer.

The measured gas may be not only a substance in the gaseous state from the start, but also a substance which is originally solid or liquid but becomes a gas due to some means or another. Further, it is also possible to connect this apparatus to another separation apparatus, for example, a gas chromatograph or liquid chromatograph, to form a gas chromatograph/mass spectrograph (GC/MS) and liquid chromatograph/mass spectrograph (LC/MS).

The configuration, shape, size, and positional relationship explained in the embodiments are shown only schematically to an extent enabling the present invention to be understood and worked. Further, the numerical values are only illustrations. Therefore, the present invention is not limited to the embodiments explained above. Various modifications are possible so long as not exceeding the gist of the technical idea shown in the claims.

The present disclosure relates to subject matter contained in Japanese Patent Application No. 2002-264551, filed on Sep. 10, 2002, the disclosure of which is expressly incorporated herein by reference in its entirety.

What is claimed is:

1. An ion attachment mass spectrometry method comprising:

generating positively charged metal ions in a metal ion generation region;

attaching the positively charged metal ions to molecules of a measured gas in an attachment region to generate attached ions; and performing mass spectrometry of the attached ions in a mass spectrometry region, wherein:

a pressure of said attachment region is set within a pressure range enabling free flight of said metal ions and said attached ions in said attachment region;

an electrostatic field is formed for decelerating said metal ions in said attachment region; and only said measured gas and the positively charged metal ions are introduced to said attachment region.

2. The ion attachment mass spectrometry method as set forth in claim 1, wherein an upper limit of said pressure range relating to the pressure of the attachment region is 10 Pa.

3. The ion attachment mass spectrometry method as set forth in claim 2, wherein said metal ions traveling in said attachment region have a translational energy not exceeding 1 eV.

4. The ion attachment mass spectrometry method as set forth in claim 1, wherein said metal ions traveling in said attachment region have a translational energy not exceeding 1 eV.

5. The ion attachment mass spectrometry method as set forth in claim 1, wherein a partition is provided between said metal ion generation region and said attachment region and the pressure of said metal ion generation region is lower than the pressure of said attachment region.

6. The ion attachment mass spectrometry method as set forth in claim 1, wherein said metal ion generation region and said mass spectrometry region are made in a common region vacuum environment.

7. The ion attachment mass spectrometry method as set forth in claim 6, wherein a path of travel of ions in said attachment region is formed as a curved path.

8. The ion attachment mass spectrometry method as set forth in claim 1, wherein all of said metal ion generation region, attachment region, and mass spectrometry region are evacuated by a single common vacuum pump.

9. The ion attachment mass spectrometry method as set forth in claim 1, wherein a mean free path of the free flight has a length of about 10 mm.

* * * * *